(12) United States Patent
Galon et al.

(10) Patent No.: US 12,373,936 B2
(45) Date of Patent: Jul. 29, 2025

(54) SYSTEM AND METHOD FOR OVERLAY METROLOGY USING A PHASE MASK (71) Applicant: KLA Corporation, Milpitas, CA (US)

(72) Inventors: Iftach Galon, Milpitas, CA (US); Itay Gdor, Tel-Aviv (IL); Yuval Lubashevsky, Haifa (IL); Yaniv Weiss, Milpitas, CA (US); Nireekshan Reddy, Milpitas, CA (US)

(73) Assignee: KLA Corporation, Milpitas, CA (US)

( * ) Notice: Subject to any disclaimer, the term of this patent is extended or adjusted under 35 U.S.C. 154(b) by 80 days.

(21) Appl. No.: 18/534,232

(22) Filed: Dec. 8, 2023

(65) Prior Publication Data
US 2025/0191170 A1 Jun. 12, 2025

(51) Int. Cl.
G06T 7/00 (2017.01)
G06T 7/70 (2017.01)

(52) U.S. Cl.
CPC .............. G06T 7/0006 (2013.01); G06T 7/70 (2017.01)

(58) Field of Classification Search
None
See application file for complete search history.

(56) References Cited

U.S. PATENT DOCUMENTS

| | | | |
|---|---|---|---|
| 10,197,389 B2 | 2/2019 | Levinski et al. | |
| 10,824,079 B2 | 11/2020 | Lubashevsky et al. | |
| 11,300,405 B2 | 4/2022 | Manassen et al. | |
| 11,346,657 B2 | 5/2022 | Manassen et al. | |
| 11,378,394 B1 | 7/2022 | Paskover et al. | |
| 2013/0044331 A1 | 2/2013 | Manassen et al. | |
| 2015/0046118 A1* | 2/2015 | Pandev | G03F 7/70641 702/155 |
| 2019/0219931 A1 | 7/2019 | Zwier | |
| 2019/0378737 A1* | 12/2019 | Gutman | H01L 21/681 |

(Continued)

FOREIGN PATENT DOCUMENTS

WO 2023027947 A1 3/2023

OTHER PUBLICATIONS

Christos Messinis, Theodorus T. M. van Schaijk, Nitesh Pandey, Vasco T. Tenner, Stefan Witte, Johannes D. de Boer, and Arie den Boef, "Diffraction-based overlay metrology using angular-multiplexed acquisition of fark-filed digital holograms," Opt. Express 28, 37419-37435 (2020) (Year: 2020).*

(Continued)

Primary Examiner — Ian L Lemieux
(74) Attorney, Agent, or Firm — Suiter Swantz IP (57) ABSTRACT An overlay metrology system is disclosed. The overlay metrology system may include a controller with one or more processors. The processors may be configured to execute program instructions causing the processors to receive pupil images of collected light from an overlay target and receive a known phase distribution to be introduced to an illumination beam directed at the overlay target. The processors may model an intensity function relating the pupil images, the known phase distribution, and one or more decentered shift parameters of structures of the overlay target. The processors may fit the pupil images to the intensity function depending on the known phase distribution and the decentered shift parameters. The processors may generate an overlay measurement based on the fit.

38 Claims, 5 Drawing Sheets (56) References Cited

U.S. PATENT DOCUMENTS

2022/0034652 A1    2/2022  Manassen et al.
2023/0314319 A1   10/2023  Manassen et al.

OTHER PUBLICATIONS

Adel et al., "Diffraction order control in overlay metrology: a review of the roadmap options," Proc. SPIE. 6922, Metrology, Inspection, and Process Control for Microlithography XXII, 692202. Apr. 2008, 20 pages.
Korean Intellectual Property Office, International Search Report and Written Opinion received in International Application No. PCT/US2024/056435, Mar. 4, 2025, 7 pages.

* cited by examiner

SYSTEM AND METHOD FOR OVERLAY METROLOGY USING A PHASE MASK

TECHNICAL FIELD

The present disclosure relates generally to overlay metrology and, more particularly, to overlay metrology of a sample using a known phase distribution of an illumination beam, such as may be introduced using a phase mask.

BACKGROUND

Overlay metrology refers to measurements of the relative alignment of layers on a sample such as, but not limited to, semiconductor devices. An overlay measurement, or a measurement of overlay error, typically refers to a measurement of the misalignment of fabricated features on two or more sample layers. Proper alignment of fabricated features on multiple sample layers is necessary for proper functioning of the device.

Demands to decrease feature size and increase feature density are resulting in correspondingly increased demand for accurate and efficient overlay metrology. Metrology systems typically generate metrology data associated with a sample by measuring or otherwise inspecting dedicated metrology targets (i.e., overlay targets) distributed across the sample. Accordingly, the sample is typically mounted on a translation stage and translated such that the metrology targets are sequentially moved into a measurement field of view.

Therefore, it is desirable to provide systems and methods for curing the above deficiencies.

SUMMARY

An overlay metrology system is disclosed in accordance with one or more illustrative embodiments of the present disclosure. In one illustrative embodiment, the overlay metrology system may include a controller with one or more processors. In another illustrative embodiment, the processors may be configured to execute program instructions causing the processors to receive pupil images of collected light from an overlay target and receive a known phase distribution to be introduced to an illumination beam directed at the overlay target. In another illustrative embodiment, the processors may model an intensity function that relates the pupil images, the known phase distribution, and one or more decentered shift parameters of structures of the overlay target. In another illustrative embodiment, the processors may fit the pupil images to the intensity function that depends on at least the known phase distribution and the one or more decentered shift parameters. In another illustrative embodiment, the processors may generate an overlay measurement based on the fit.

In a further aspect, the overlay target may be a single cell overlay target. In another aspect, the fit may include a linear-regression pattern fitting. In another aspect, the fit may include a first pattern fitting and a second pattern fitting, where the first pattern fitting is based on a first order diffraction overlap region of the pupil images, and the second pattern fitting is based on a second order diffraction overlap region of the pupil images. In another aspect, the fit may be based on calibrating a phase mask configured to cause the known phase distribution. In another aspect, the overlay target may include a Moiré fringe overlay target. In another aspect, the system may further include performing a defocus adjustment of the overlay target, where the fit is based on the amount of the defocus adjustment performed, and the known phase distribution is based on the amount of the defocus adjustment performed. In another aspect, receiving the pupil images may include performing a plurality of defocus adjustments of the overlay target. In another aspect, receiving the pupil images may include receiving a plurality of pupil images of a plurality of spot locations of a cell of the overlay target, and the fit may be based on the plurality of pupil images. In another aspect, the known phase distribution may include an F1 type phase distribution which is wavelength-independent and characterizable in a form of at least one of $F\_1(NA\_x, NA\_y) = NA\_x\ NA\_y + \text{constant}$; or $F\_1(NA\_x, NA\_y) = NA\_x |NA\_y| + \text{constant}$. In another aspect, the introduction of the known phase distribution to the illumination beam may be performed via a phase mask of the F1 type phase distribution of the system. In another aspect, the fit of the pupil images to the intensity function may be performed simultaneously for a +1 first order diffraction intensity function and a −1 first order diffraction intensity function for the F1 type phase distribution. In another aspect, the known phase distribution may include an F2 type phase distribution which is wavelength-independent and characterizable in a form of at least one of $F\_2(NA\_x, NA\_y) = NA\_x\hat{\ } + \text{constant}$; or $F\_2(NA\_x, NA\_y) = NA\_x\hat{\ } + NA\_y\hat{\ }2 + \text{constant}$. In another aspect, the introduction of the known phase distribution to the illumination beam may be performed via a phase mask of the F2 type phase distribution of the system. In another aspect, the fit of the pupil images to the intensity function may be performed sequentially for a +1 first order diffraction intensity function and a −1 first order diffraction intensity function for the F2 type phase distribution. In another aspect, the phase mask of the F2 type phase distribution may include at least one of a toric lens, a cylindrical plano-convex lens, or a defocused pupil-plane apodizer. In another aspect, the fit of the pupil images may include multiple fits configured to simultaneously solve for an effective mask height (nh), an optical stack thickness (A), and the overlay measurement, the multiple fits scanning a parameter space of the nh and the A.

An overlay metrology system is disclosed in accordance with one or more illustrative embodiments of the present disclosure. In one illustrative embodiment, the overlay metrology system may include an optical sub-system. In another illustrative embodiment, the optical sub-system may include an illumination source configured to generate an illumination beam. In another illustrative embodiment, the system may include an objective lens configured to direct the illumination beam comprising a known phase distribution to an overlay target of a sample. In another illustrative embodiment, the system may include a phase mask configured to cause the known phase distribution in a portion of the illumination beam. In another illustrative embodiment, the system may include a detector configured to receive pupil images of collected light emanating from the overlay target. In another illustrative embodiment, the system may include a controller communicatively coupled to the detector. In another illustrative embodiment, the controller may include one or more processors configured to execute program instructions causing the processors to receive the pupil images of the collected light emanating from the overlay target and receive a known phase distribution to be introduced to an illumination beam directed at the overlay target. In another illustrative embodiment, the processors may model an intensity function that relates the pupil images, the known phase distribution, and one or more decentered shift parameters of structures of the overlay target. In another illustrative embodiment, the processors may fit the pupil images to the intensity function that depends on at least the known phase distribution and the decentered shift parameters of structures of the overlay target. In another illustrative embodiment, the processors may generate an overlay measurement based on the fit.

A method for overlay metrology is disclosed in accordance with one or more illustrative embodiments of the present disclosure. In one illustrative embodiment, the method may include directing an illumination beam comprising a known phase distribution to illuminate an overlay target. In another illustrative embodiment, the method may include receiving pupil images of collected light emanating from the overlay target. In another illustrative embodiment, the method may include modeling an intensity function that relates the pupil images, the known phase distribution, and one or more decentered shift parameters of structures of the overlay target. In another illustrative embodiment, the method may include fitting the pupil images to the intensity function that depends on at least the known phase distribution and the one or more decentered shift parameters of structures of the overlay target. In another illustrative embodiment, the method may include generating an overlay measurement based on the fit.

In a further aspect, the overlay target may be a single cell overlay target. In another aspect, the fit may include a linear-regression pattern fitting. In another aspect, the fit may include a first pattern fitting and a second pattern fitting, where the first pattern fitting is based on a first order diffraction overlap region of the pupil images, and the second pattern fitting is based on a second order diffraction overlap region of the pupil images. In another aspect, a single fitting may be based on a combination of the first order diffraction overlap region and the second order diffraction overlap region. In another aspect, the fit may be based on calibrating a phase mask configured to cause the known phase distribution. In another aspect, the overlay target may include a Moiré fringe overlay target. In another aspect, the method may further include performing a defocus adjustment of the overlay target, where the fit is based on the amount of the defocus adjustment performed, and the known phase distribution is based on the amount of the defocus adjustment performed. In another aspect, receiving the pupil images may include performing a plurality of defocus adjustments of the overlay target. In another aspect, receiving the pupil images may include receiving a plurality of pupil images of a plurality of spot locations of a cell of the overlay target, and the fit may be based on the plurality of pupil images. In another aspect, the known phase distribution may include an F1 type phase distribution which is wavelength-independent and characterizable in a form of at least one of $F\_1(NA\_x, NA\_y) = NA\_x\ NA\_y + \text{constant}$; or $F\_1(NA\_x, NA\_y) = NA\_x |NA\_y| + \text{constant}$. In another aspect, the introduction of the known phase distribution to the illumination beam may be performed via a phase mask of the F1 type phase distribution of the system. In another aspect, the known phase distribution may include an F2 type phase distribution which is wavelength-independent and characterizable in a form of at least one of $F\_2(NA\_x, NA\_y) = NA\_x\hat{\ } + \text{constant}$; or $F\_2(NA\_x, NA\_y) = NA\_x\hat{\ } + NA\_y\hat{\ } + \text{constant}$.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures.

DETAILED DESCRIPTION

The present disclosure has been particularly shown and described with respect to certain embodiments and specific features thereof. The embodiments set forth herein are taken to be illustrative rather than limiting. It should be readily apparent to those of ordinary skill in the art that various changes and modifications in form and detail may be made without departing from the spirit and scope of the disclosure. Reference will now be made in detail to the subject matter disclosed, which is illustrated in the accompanying drawings.

Referring to FIGS. 1A through 3, systems and methods for overlay metrology including fitting pupil images to an intensity function are disclosed, in accordance with one or more embodiments of the present disclosure.

Embodiments of the present disclosure are directed to initiating a (known) phase modulation to an illumination beam directed at a target of a sample and fitting pupil images from light emanating from the target to an intensity function to determine overlay. For example, a phase mask may be used to introduce a known phase distribution, which may cause (measured) pupil images (e.g., pupil plane image of collected light emanating from the sample) to correlate with the overlay of the overlay target. For instance, the system and method may fit the pupil images to an intensity function that is a function of the known phase distribution and grating structures of the target. In embodiments, the closer the fit, the closer the overlay is to a given value. Specific amounts of phase modulations in the light directed at the sample may generate specific pupil images based on specific grating structures of the target, which may be used in a comparison/fit operation to determine the amount of overlay.

It is contemplated herein that a phase mask (e.g., phase-masked apodizer) may be implemented using various overlay metrology target designs, measurement techniques, and corresponding optical sub-systems.

In embodiments, an image-based optical sub-system includes a phase mask in an illumination pupil. For example, image-based optical sub-systems may illuminate an overlay target (e.g., a grating over grating target, a box-in-box metrology target, or the like) and capture an overlay signal including pupil images of the overlay target.

For other techniques of determining overlay-which do not necessarily apply here but may illustrate differences-scanning-based scatterometry measurement techniques may be used with fast photodetectors in selected locations of a collection pupil to capture time-varying interference signals generated as the sample is in continuous motion and scanned with respect to an illumination beam. Various non-limiting scanning scatterometry overlay metrology techniques are described in U.S. Patent Publication No. 2022/0034652 filed on Feb. 17, 2021; and U.S. patent application Ser. No. 17/119,536 filed on Dec. 11, 2020, which are all incorporated herein by reference in their entireties. For example, fast photodetectors may be placed at locations of overlap between selected diffraction orders to capture time-varying interference signals in these regions. On the other hand, it is contemplated in embodiments herein that a phase mask in an illumination pupil of a static (i.e., non-scanning) optical sub-system, if the phase modulation is expressive enough, may enable fast and robust overlay measurements using a single cell.

Figure 1A:
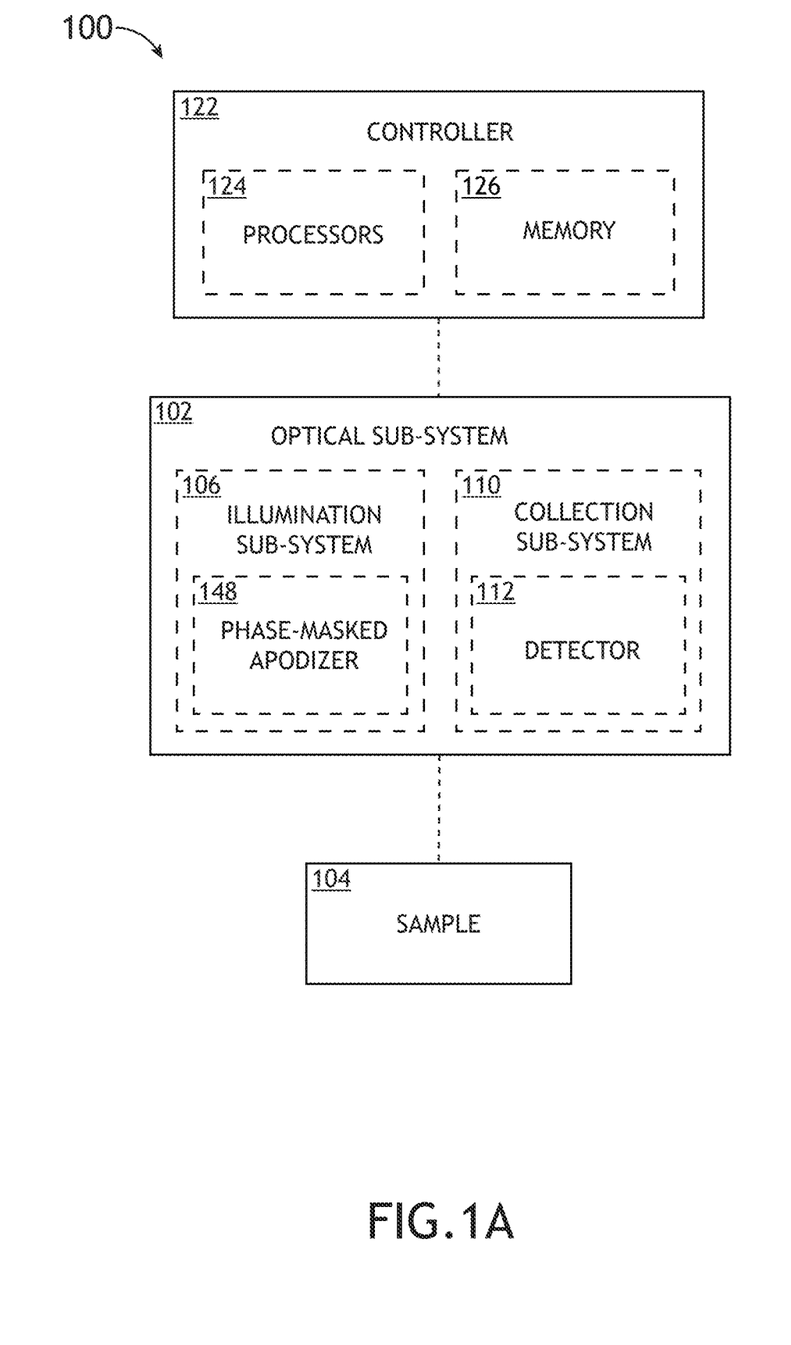
FIG. 1A is a conceptual view of a system for overlay metrology, in accordance with one or more embodiments of the present disclosure.

FIG. 1A is a conceptual view of a system 100 for overlay metrology, in accordance with one or more embodiments of the present disclosure.

In embodiments, the system 100 includes an optical sub-system 102 to perform overlay measurements on sample 104.

In embodiments, the system 100 includes a controller 122 communicatively coupled to the optical sub-system 102. The controller 122 may include one or more processors 124 and a memory device 126, or memory. For example, the one or more processors 124 may be configured to execute a set of program instructions maintained in the memory device 126.

Figure 1B:
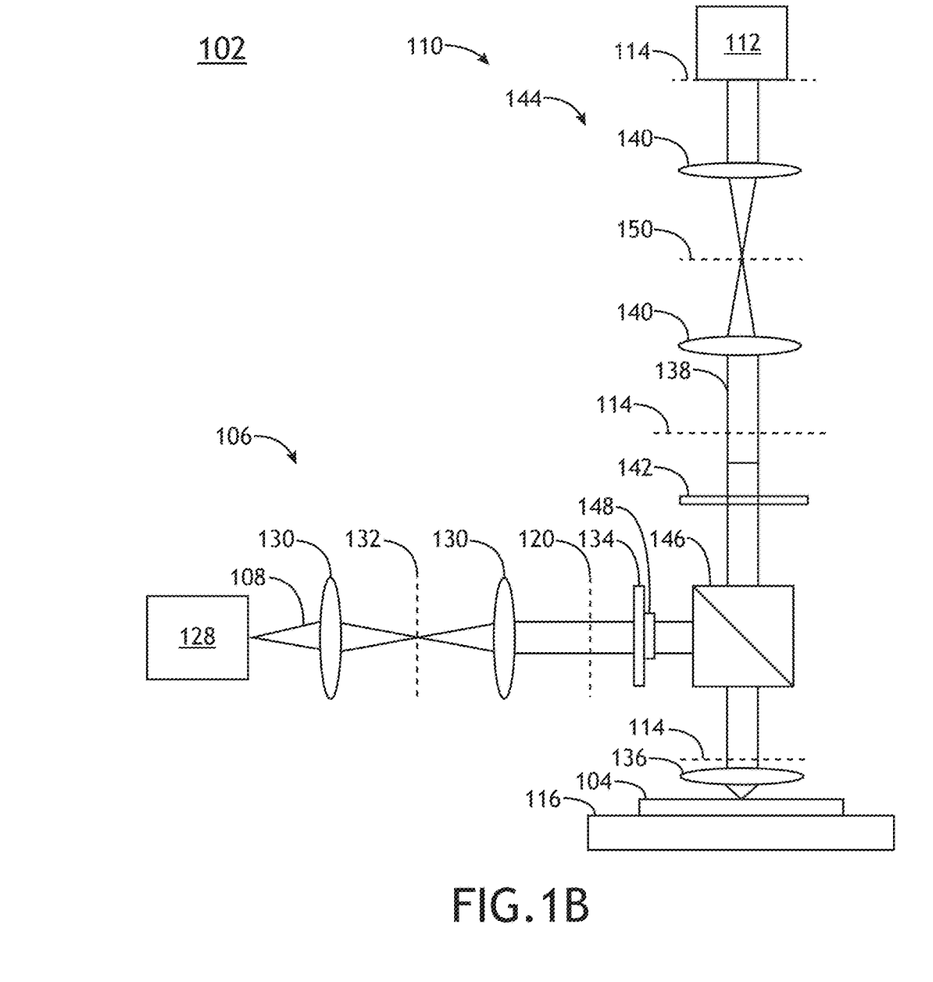
FIG. 1B is a schematic view of the optical sub-system with a phase mask in an illumination pupil plane, in accordance with one or more embodiments of the present disclosure.

FIG. 1B is a schematic view of the optical sub-system 102 with a phase mask 148 in an illumination pupil plane 120, in accordance with one or more embodiments of the present disclosure. For example, the phase mask 148 of FIG. 1A may be the same phase mask 148 as shown in FIG. 1B.

In embodiments, the system 100 includes a detector 112. Unless noted otherwise, the one or more detectors 112 may be used for static overlay metrology and be positioned in a collection pupil plane 114 and/or outside a collection field plane 150 (e.g., near a collection pupil plane 114). The detector 112 may include any type of optical detector known in the art suitable for capturing light. For example, the detector 112 may include a multi-pixel detector such as a complementary metal-oxide semiconductor (CMOS) detector, a charge-coupled device (CCD) detector, or the like.

In embodiments, the optical sub-system 102 may include a translation stage 116 to move the sample 104 through a measurement field of view of the optical sub-system 102.

In embodiments, the optical sub-system 102 may perform scatterometry overlay measurements on portions of the sample 104 having overlay targets such as, but not limited to, grating-over-grating structures.

In embodiments, the optical sub-system 102 includes an illumination sub-system 106 and a collection sub-system 110. The phase mask 148 may be located at a first pupil plane (e.g., any illumination pupil plane 120 such as before and/or after the objective lens 136, but before the sample 104). The one or more detectors 112 may be located at a second pupil plane (e.g., any collection pupil plane 114 after the sample 104).

In embodiments, the overlay metrology system 100 (or optical sub-system 102) includes an illumination sub-system 106 configured to generate illumination in the form of one or more illumination beams 108 to illuminate the sample 104 and a collection sub-system 110 to collect collected light 138 from the illuminated sample 104. Further, the one or more illumination beams 108 may be spatially limited such that they illuminate selected portions of the sample 104. For instance, each of the one or more illumination beams 108 may be spatially limited to illuminate a particular overlay target 202.

System 100 may be configured for certain types of samples or features of a sample 104 according to a "metrology recipe." For instance, the system 100 may be programmed to calculate overlay measurements of certain types of features according to a metrology recipe (e.g., methodology, process, program instructions, and/or the like).

Figure 2:
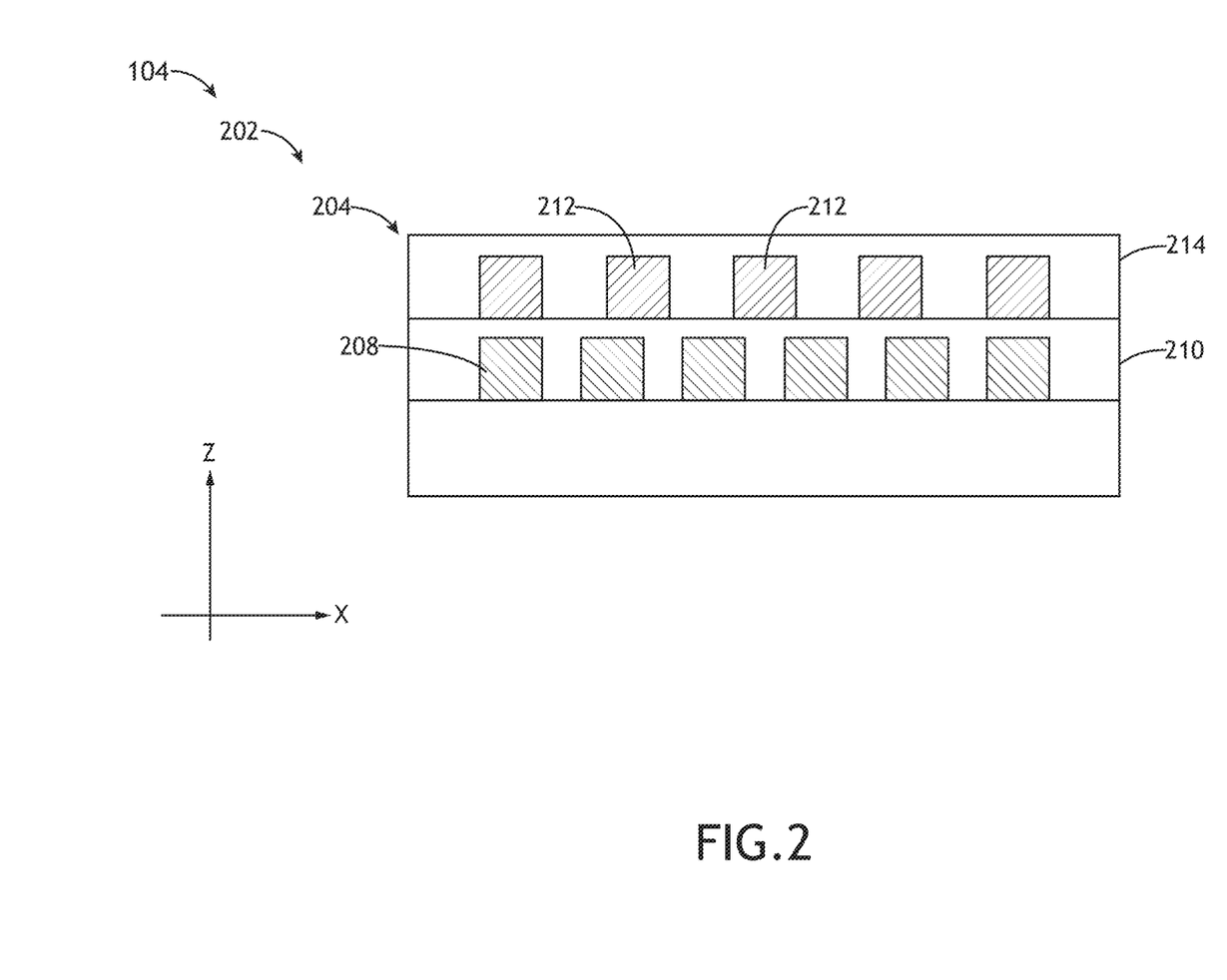
FIG. 2 is a side view of a single cell of an overlay target of a sample, in accordance with one or more embodiments of the present disclosure.

FIG. 2 is a side view of a single cell 204 of an overlay target 202 of a sample 104, in accordance with one or more embodiments of the present disclosure in the context of scatterometry overlay metrology.

In embodiments, the grating structures on the two layers (e.g., first layer 210 and second layer 214) of the sample 104 in the overlay target 202 have a common pitch (e.g., periodic distance between elements 212).

In embodiments, the grating structures on the two layers of the sample 104 in the overlay target have different pitches, wherein the grating-over-grating structures form Moiré structures (as shown in FIG. 2).

In embodiments, the cell 204 includes first-layer printed elements 208 located on a first layer 210 of the sample 104 and second-layer printed elements 212 located on a second layer 214 of the sample 104 oriented such that the regions including the first-layer printed elements 208 and the second-layer printed elements 212 overlap to form a grating-over-grating structure. Further, as illustrated in FIG. 2, the first-layer printed elements 208 may be, but are not required to be, designed to include an intended offset (due to different pitches) from the second-layer printed elements 212 along the X-direction by a selected amount.

Many scatterometry overlay metrology techniques determine overlay by illuminating an overlay target having grating structures in two layers (e.g., grating-over-grating structures), where an overlay measurement is based on asymmetries between positive (e.g., +1) and negative (e.g., −1) diffraction orders. For example, various scatterometry techniques are described in U.S. patent application Ser. No. 17/068,328 filed on Oct. 12, 2020; U.S. Pat. No. 10,824,079 issued on Nov. 3, 2020; U.S. Pat. No. 10,197,389 issued on Feb. 9, 2019; and Adel, et al., "Diffraction order control in overlay metrology: a review of the roadmap options," Proc. SPIE. 6922, Metrology, Inspection, and Process Control for Microlithography XXII, 692202. (2008); all of which are incorporated herein by reference in their entireties. It is contemplated herein that a phase mask located in an illumination pupil of a scatterometry optical sub-system may enable calibrated pattern matching of phase patterns.

It is to be understood, however, that the overlay target 202 in FIG. 2 (and elements in related FIG. 3) and the associated descriptions are provided solely for illustrative purposes and should not be interpreted as limiting. Rather, the overlay target 202 may include any suitable design (e.g., grating-over-grating overlay target design, grating next to grating, three-layer grating).

Figure 3:
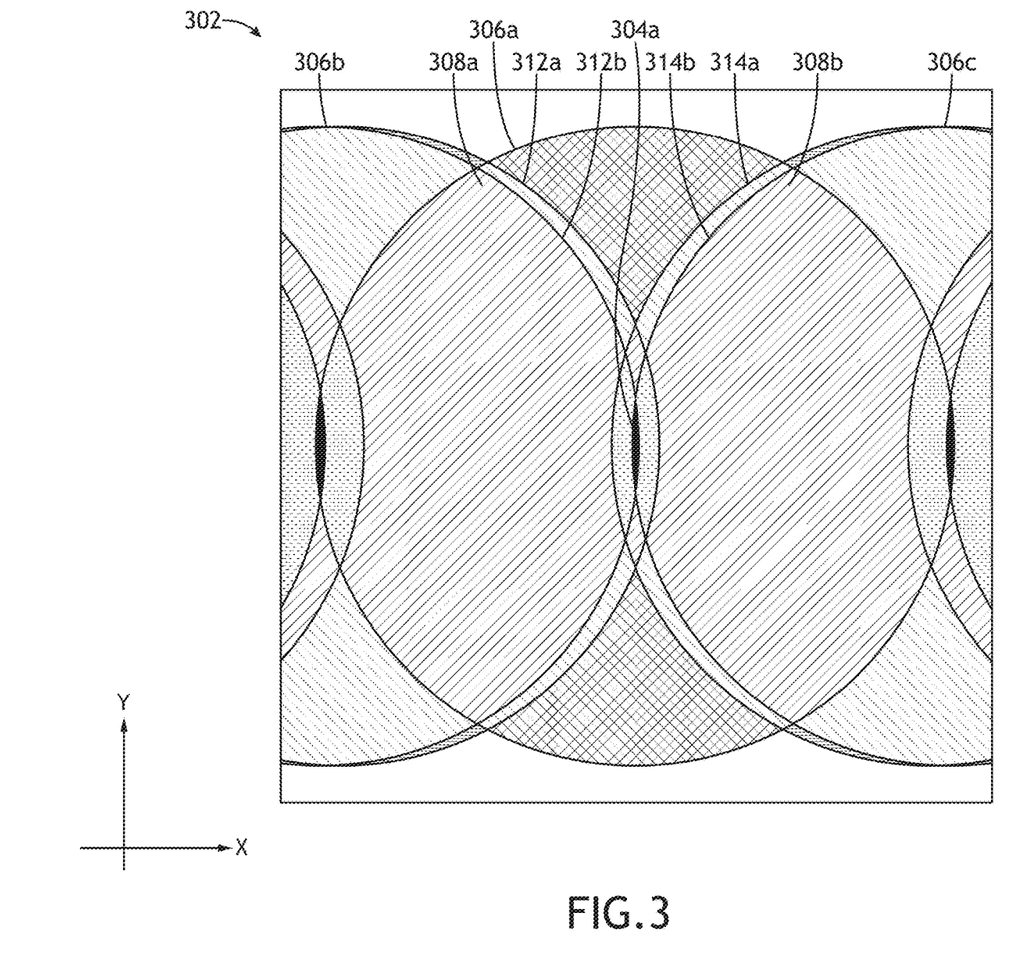
FIG. 3 is a conceptual view of a collection pupil plane distribution of diffraction orders, in accordance with one or more embodiments of the present disclosure.

FIG. 3 illustrates a conceptual view of a collection pupil plane distribution 302, in accordance with one or more embodiments of the present disclosure.

An example of overlapping diffraction orders 308a and 308b is shown in FIG. 3. It is recognized herein that the distribution of diffracted orders of an illumination beam 108 by a periodic structure (such as a grating-over-grating structure) may be influenced by a variety of parameters such as, but not limited to a wavelength of the illumination beam 108, an incidence angle of the illumination beam 108 in both altitude and azimuth directions, a period of the periodic structures (i.e., pitch), or a numerical aperture (NA) of a collection lens. Accordingly, in embodiments, the illumination sub-system 106, the collection sub-system 110, and the overlay target 202 may be configured to provide an overlapping distribution of zero-order diffraction and first-order diffraction in the collection pupil plane 114 of the collection sub-system 110. For example, the illumination sub-system 106 and/or the collection sub-system 110 may be configured to generate measurements on grating-over-grating structures having a selected range of periodicities that provide the overlapping distribution. Further, various components of the illumination sub-system 106 and/or the collection sub-system 110 (e.g., stops, pupils, or the like) may be adjustable to provide the overlapping distribution for a given structure (e.g., grating-over-grating) with a given periodicity.

The collection sub-system 110 may collect at least one of 0-order diffraction 306a (e.g., specular reflection), and +/−1 first diffraction orders 306b, 306c from the sample 104 associated with diffraction of the illumination beam 108. Further, the collection sub-system 110 may include one or more detectors 112 configured to image the collection pupil plane 114 at locations including regions of overlap between the 0-order diffraction, the +/−1 first diffraction orders, and/or the +/− second diffraction orders. Phase changes initiated by the phase mask 148 may cause patterns in the image which may be compared to determine the overlay.

In embodiments, the optical sub-system 102 includes an objective lens 136 to focus the illumination beam 108 onto the sample 104 (e.g., an overlay target 202 with overlay target elements located on two or more layers of the sample 104). For example, the objective lens 136 may be configured to collect measurement light emanating from a sample 104 in response to the illumination beam 108 according to a metrology recipe. For instance, as shown in FIG. 2, the sample 104 may include an overlay target 202 formed from a cell 204 that includes a grating-over-grating structure formed from grating structures 212, 208 on two layers 210, 214 of the sample 104.

In embodiments, the illumination beam 108 of system 100 is circular. FIG. 3 is in relation to diffraction orders corresponding to a circular illumination beam. In embodiments, the illumination sub-system 106 illuminates the overlay target 202 with one or more illumination beams 108 at normal incidence (or near-normal incidence). Further, the one or more illumination beams 108 may illuminate the overlay target 202 with a limited range of incidence angles as illustrated by the limited size of the distribution 302 of the collection pupil plane 114 in FIG. 3. In this regard, the overlay target 202 may diffract the one or more illumination beams 108 into discrete diffraction orders 306 (306a, 306b, 306c).

The circular illumination beam forms circular diffraction orders in a collection pupil plane 114 as shown in FIG. 3 by zero order (0) circular diffraction order 306a, first order (+1) circular diffraction order 306c, and first order (−1) circular diffraction order 306b when an overlay target 202 is illuminated by the circular illumination beam.

For a Moiré fringe overlay target 202 (e.g., different pitches for gratings 208, 212 in different layers), the different pitches may produce slightly offset diffraction orders. The two diffraction orders 312a, 312b correspond to two different pitches of the first order (−1) circular diffraction order 306b. The two diffraction orders 314a, 314b correspond to two different pitches of the first order (+1) circular diffraction order 306c. However, a Moiré configuration is merely a nonlimiting example for illustrative purposes, and at least some embodiments herein may use common pitches of gratings 208, 212.

Overlapping first diffraction order 304a (e.g., the +1 and −1 are overlapping in the center) is also shown.

The system 100 may include a phase mask 148. The phase mask 148 may be configured to modulate a phase distribution according to a function. Note that the phase masks 148 and equation forms described below are nonlimiting and for illustrative purposes and any phase mask 148 and/or equation form that is expressive enough may be used. The phase mask 148 provides a known phase function that may impact a pupil plane image in a known way, which may be exploited to provide sensitive metrology measurements. For example, the phase mask 148 may be configured to modulate the phase distribution according to a function that varies across the pupil plane (e.g., F(x-coordinate, y-coordinate)). For instance, the phase mask 148 may be a variable-thickness piece of glass with refractive index (n). In embodiments, the phase mask 148 may include toric lenses, cylindrical plano-convex lenses, and/or the like. In this way, the phase mask 148 may allow for selectively modulating specific/selected portions of the phase distribution of illumination beam in the illumination pupil plane. The phase mask 148 may also be implemented via phase-shifting films or coatings, where the phase shift is introduced by varying the optical path length via changes in film or coating thickness. These films or coatings can be deposited on a substrate, such as a transparent glass, to create the phase mask 148. Note these are non-limiting examples of a phase mask 148, and a wide range of other optical components may also be used as phase masks such as, but not limited to, crystals, diffractive elements, Fresnel lenses, and/or the like. The phase mask 148 may include multiple components, each with one or more constant and/or variable refractive indices and/or adjustments to optical path length such that a combined effect is a change in phase distribution of the light.

Furthermore, the use of a phase mask 148 may be particularly useful in systems 100 where the light source 128 is coherent or partially coherent.

The following formulas relate to an overlay target with two or more layers, such as shown in FIG. 2, with a first (top) layer with a first pitch ($P_T$) and a second (lower) layer with a second pitch ($P_B$). In embodiments, any first pitch ($P_T$) and second pitch ($P_B$) may be used, such as different pitches of a Moiré overlay target 202, or common/equal pitches of a common-pitch overlay target 202. For example, at least one of the Moiré overlay target 202, or a common-pitch overlay target 202 may be used.

Consider an overlay target with periodicity in the x-direction. The intensity measured at the pupil plane 114 (e.g., where the detector 112 is) in the overlap between zero and first-order diffraction of +1 (i.e., +1 first order diffraction intensity function) is:

$$I^{0+1} = DC + 2A_{T0}A_{T+1} \qquad \text{(Eq. 1)}$$
$$\cos\left(2\pi\left(\frac{nh}{\lambda}\left(F(-NA_x, -NA_y) - F\left(-NA_x + \frac{\lambda}{P_T}, -NA_y\right)\right)\right) + \frac{x_T}{P_T}\right) +$$
$$2A_{B0}A_{T0}\cos(4\pi H_0) + 2A_{B0}A_{B+1}\cos$$

-continued $$\left(2\pi\left(H_0 - H_{+1} + \frac{nh}{\lambda}\left(F(-NA_x, -NA_y) - F\left(-NA_x + \frac{\lambda}{P_B}, -NA_y\right)\right)\right) + \frac{x_B}{P_B}\right) + 2A_{B0}A_{T+1}$$

$$\cos\left(2\pi\left(2H_0 + \frac{nh}{\lambda}\left(F(-NA_x, -NA_y) - F\left(-NA_x + \frac{\lambda}{P_T}, -NA_y\right)\right)\right) + \frac{x_T}{P_T}\right) + 2A_{B+1}A_{T0}\cos$$

$$\left(2\pi\left(H_0 + H_{+1} + \frac{nh}{\lambda}\left(F(-NA_x, -NA_y) - F\left(-NA_x + \frac{\lambda}{P_B}, -NA_y\right)\right)\right) - \frac{x_B}{P_B}\right) + 2A_{B+1}A_{T+1}\cos\left(2\pi\left(H_0 + H_{+1} + \frac{nh}{\lambda}\left(F\left(-NA_x + \frac{\lambda}{P_B}, -NA_y\right) - F\left(-NA_x + \frac{\lambda}{P_T}, -NA_y\right)\right)\right) + \frac{x_T}{P_T} - \frac{x_B}{P_B}\right)$$

The intensity measured in the overlap between zero and first-order diffraction of −1 (i.e., −1 first order diffraction intensity function) is:

$$I^{0-1} = DC + 2A_{T0}A_{T-1} \quad \text{(Eq. 2)}$$

$$\cos\left(2\pi\left(\frac{nh}{\lambda}\left(F(-NA_x, -NA_y) - F\left(-NA_x - \frac{\lambda}{P_T}, -NA_y\right)\right)\right) + \frac{x_T}{P_T}\right) +$$

$$2A_{B0}A_{T0}\cos(4\pi H_0) + 2A_{B0}A_{B-1}\cos$$

$$\left(2\pi\left(H_0 - H_{-1} + \frac{nh}{\lambda}\left(F(-NA_x, -NA_y) - F\left(-NA_x - \frac{\lambda}{P_B}, -NA_y\right)\right)\right) - \frac{x_B}{P_B}\right) + 2A_{B0}A_{T-1}$$

$$\cos\left(2\pi\left(2H_0 + \frac{nh}{\lambda}\left(F(-NA_x, -NA_y) - F\left(-NA_x - \frac{\lambda}{P_T}, -NA_y\right)\right)\right) - \frac{x_T}{P_T}\right) + 2A_{B-1}A_{T0}\cos$$

$$\left(2\pi\left(H_0 + H_{-1} + \frac{nh}{\lambda}\left(F(-NA_x, -NA_y) - F\left(-NA_x - \frac{\lambda}{P_B}, -NA_y\right)\right)\right) + \frac{x_B}{P_B}\right) + 2A_{B-1}A_{T-1}\cos\left(2\pi\left(H_0 + H_{-1} + \frac{nh}{\lambda}\left(F\left(-NA_x - \frac{\lambda}{P_B}, -NA_y\right) - F\left(-NA_x - \frac{\lambda}{P_T}, -NA_y\right)\right)\right) - \frac{x_T}{P_T} + \frac{x_B}{P_B}\right)$$

where $A_{T0}$, $A_{T\pm1}$, $A_{B0}$, $A_{B\pm1}$ are the amplitudes associated with the top grating zero and first orders, and the bottom grating zero and first orders, respectively; $NA_x$, $NA_y$, are the NA-pupil coordinates; and DC is a constant analogous to no interference (e.g., a lack of intensity modulation). $x_T$ and $x_B$ are the shifts from the center of symmetry of the top and bottom grating structures, respectively, of an overlay target and may be referred to as decentered shift parameters. Functions of the form F(may be known phase distributions inserted into the illumination beam 108 before reaching the sample.

$NA_x$ and $NA_y$ represent the numerical aperture (NA) pupil coordinates in the x and y directions, respectively. In an optical system, the numerical aperture is a dimensionless number that characterizes the range of angles over which the system can accept or emit light. By incorporating these parameters into phase-mask functions (e.g., F1 and F2 described below), how light spreads may be accurately modeled from the overlay target to the detector. Note that the equation forms (e.g., F1 and F2) are nonlimiting and any equation form that is expressive enough may be used. The procedure above works for any, sufficiently expressive, phase mask $F(NA_x, NA_y)$. Typically, though, the phase differences in $I^{0\pm1}$ are wavelength dependent, and this may need to be accounted for in the calibration procedure.

The defocus adjustment optical path difference (OPD) phase factors are given by:

$$H_0 = \frac{\Delta}{\lambda}\sqrt{1 - NA_x^2 - NA_y^2} \quad \text{(Eq. 3)}$$

$$H_{\pm1} = \frac{\Delta}{\lambda}\sqrt{1 - \left(NA_x \pm \frac{\lambda}{P_B}\right)^2 - NA_y^2} \quad \text{(Eq. 4)}$$

where $\Delta$ is the optical stack thickness, J is the wavelength, and $P_T$, $P_B$ are pitches for the top and bottom gratings, respectively.

The local phase on the illumination pupil which is induced by the phase-mask is given by:

$$\text{Exp}\left(\frac{2\pi i}{\lambda}nhF(NA_x, NA_y)\right) \quad \text{(Eq. 5)}$$

where the local phase-function $F(NA_x, NA_y)$ is real, and n h is the characteristic optical thickness of the mask (n is the diffraction index of the mask material, and h is a characteristic height), the sought-out parameters $x_T$ and $x_B$ are the shifts from the center of symmetry of the top and bottom gratings, respectively, and the desired overlay is given by:

$$ovl = x_B - x_T \quad \text{(Eq. 6)}$$

By breaking up each of the cosine terms in $I^{0\pm1}$ ($\cos(\alpha+\beta)=\cos(\alpha)\cos(\beta)-\sin(\alpha)\sin(\beta)$), the $x_T$, $x_B$-dependent terms may be factored out as the coefficients of functions of pupil coordinates. The pupil coordinate functions may then be used as features in a fit to the pupil image data. The fit results give $x_T$, $x_B$ (or their linear combinations) as functions of the fit coefficients (e.g., typically, arctan functions of fit coefficient ratios times $$\frac{P_{T,B}}{2\pi}\text{)}.$$

For two types of phase masks 148 the wavelength dependence of the phase-differences in $I^{0\pm1}$ can be eliminated, providing wavelength independent phase masks. For gratings with x-periodicity (bars along the y-direction or "y-gratings") these two types of wavelength independent phase masks (i.e., F1 type phase distribution and F2 type phase distribution) are characterizable in the forms:

$$F_1(NA_x, NA_y) = NA_x g_1(NA_y) + \text{constant} \quad \text{(Eq.7)}$$

and $$F_2(NA_x, NA_y) = NA_x^2 + g_2(NA_y) + \text{constant} \quad \text{(Eq.8)}$$

where $g_1$ is any non-trivial (constant) function and $g_2$ is any function. For y-periodicity (bars along the x-direction or "x-gratings"), then exchange $NA_x \Leftrightarrow NA_y$.

In embodiments, the introduction of the known phase distribution to the illumination beam is performed via a phase mask of the F1 type phase distribution of the system. The fit of the pupil images to the intensity function may be performed simultaneously for a +1 first order diffraction intensity function (e.g., Eq. 1) and a −1 first order diffraction intensity function (e.g., Eq. 2) for the F1 type phase distribution.

In embodiments, the introduction of the known phase distribution to the illumination beam is performed via a phase mask of the F2 type phase distribution of the system. The fit of the pupil images to the intensity function could be performed sequentially for a +1 first order diffraction intensity function and a −1 first order diffraction intensity function for the F2 type phase distribution. The phase mask of the F2 type phase distribution may include at least one of (e.g., any one individually): a toric lens; a cylindrical plano-convex lens; or a defocused pupil-plane apodizer (e.g., using defocus adjustments to introduce a variety of known phase distributions to generate the overlay measurement).

For these cases, the phase-difference in $1^{0\pm1}$ may be linear functions of pupil coordinates which are wavelength independent.

For a phase-mask choice of the $F_1$, $F_2$-type, the pupil-image data can be fit (for example by means of linear-regression), to the linear combination:

$$A^C_{\emptyset_T}\cos(\emptyset_T) + A^S_{\emptyset_T}\sin(\emptyset_T) + \qquad \text{(Eq. 9)}$$
$$A^C_{\emptyset_{0T}}\cos(\emptyset_0 \pm \emptyset_T) \pm A^S_{\emptyset_{0T}}\sin(\emptyset_0 \pm \emptyset_T) + A^C_{\emptyset_{B_m}}\cos(\emptyset_{B_m}) +$$
$$A^S_{\emptyset_{B_m}}\sin(\emptyset_{B_p}) + A^C_{\emptyset_{B_p}}\cos(\emptyset_{B_p}) \pm A^S_{\emptyset_{B_p}}\sin(\emptyset_{B_m}) +$$
$$A^C_{\emptyset_M}\cos(\emptyset_M) + A^S_{\emptyset_M}\sin(\emptyset_M) + A^C_{\emptyset_0}\cos(\emptyset_0) + \text{constant}$$

where the phases are:

$$\emptyset_{B_p} = \pm 2\pi(H_0 + H_{\pm 1} \pm nhf_B) \qquad \text{(Eq. 10)}$$

$$\emptyset_{B_m} = \pm 2\pi(-H_0 + H_{\pm 1} \pm nhf_B) \qquad \text{(Eq. 11)}$$

$$\emptyset_M = \pm 2\pi(H_0 + H_{\pm 1} \pm nhf_M) \qquad \text{(Eq. 12)}$$

$$\emptyset_T = 2\pi(nhf_T) \qquad \text{(Eq. 13)}$$

$$\emptyset 0 = 4\pi H_0 \qquad \text{(Eq. 14)}$$

where the ±corresponds to 0+1 and 0−1 diffraction order overlap regions 308a, 308b.

The spatial frequencies are given by:

$$f_T = \frac{\text{var}}{P_T},\ f_B = \frac{\text{var}}{P_B},\ f_M = \text{var}\left(\frac{1}{P_T} - \frac{1}{P_B}\right) \qquad \text{(Eq. 15 – 17)}$$

where var is a function of pupil coordinates given by:

$$\text{var} = \begin{cases} g_1(-NA_y) & \text{for } F_1 \\ -2NA_x & \text{for } F_2 \end{cases} \qquad \text{(Eq. 18)}$$

For the $F_1$ case, the fit is performed simultaneously to the $1^{0+1}$ and $1^{0-1}$ images, and the values of $x_T$ and $x_B$ are obtained from the fit results using:

$$x_T = \frac{P_T}{2\pi}\arctan\left(\frac{A^s_{\emptyset_T}}{A^c_{\emptyset_T}}\right),\ x_T = \frac{P_T}{2\pi}\arctan\left(\frac{A^s_{\emptyset_T}}{A^c_{\emptyset_T}}\right), \qquad \text{(Eq. 19 – Eq. 23)}$$

$$x_B = \frac{P_B}{2\pi}\arctan\left(\frac{A^s_{\emptyset_{B_m}}}{A^c_{\emptyset_{B_m}}}\right) x_B = \frac{P_B}{2\pi}\arctan\left(\frac{A^s_{\emptyset_{B_p}}}{A^c_{\emptyset_{B_p}}}\right),$$

$$\frac{x_B}{P_B} - \frac{x_T}{P_T} = \arctan\left(\frac{A^s_{\emptyset_M}}{A^c_{\emptyset_M}}\right)$$

For the $F_2$ case, the $1^{0+1}$ and $1^{0-1}$, which could be fit separately, one obtains:

$$x_T \mp \frac{nh\lambda}{P_T} = \frac{P_T}{2\pi}\arctan\left(\frac{A^{s\pm}_{\emptyset_T}}{A^{c\pm}_{\emptyset_T}}\right), \qquad \text{(Eq. 24 – Eq. 28)}$$

$$x_T \mp \frac{nh\lambda}{P_T} = \frac{P_T}{2\pi}\arctan\left(\frac{A^{s\pm}_{\emptyset_{oT}}}{A^{c\pm}_{\emptyset_{oT}}}\right),$$

$$x_B \mp \frac{nh\lambda}{P_T} = \frac{P_B}{2\pi}\arctan\left(\frac{A^{s\pm}_{\emptyset_{B_m}}}{A^{c\pm}_{\emptyset_{B_m}}}\right),$$

$$x_B \mp \frac{nh\lambda}{P_T} = \frac{P_B}{2\pi}\arctan\left(\frac{A^{s\pm}_{\emptyset_{B_p}}}{A^{c\pm}_{\emptyset_{B_p}}}\right),$$

$$\frac{x_B}{P_B} - \frac{x_T}{P_T} \mp nh\lambda\left(\frac{1}{P_T^2} - \frac{1}{P_B^2}\right) = \arctan\left(\frac{A^{s\pm}_{\emptyset_M}}{A^{c\pm}_{\emptyset_M}}\right)$$

Each pair is then averaged between the $1^{0+1}$ and $1^{0-1}$ results in order to remove the constant terms.

For the case of $P_T = P_B = P$, some fit features are degenerate, but otherwise, the analysis may follow a similar process.

Examples of phase masks 148 (e.g., characterizable forms of F1 and F2) which may be constructed from materials with refractive index n (such as glass) include, but are not limited to equations in the characterizable forms of:

$$F_1(NA_x, NA_y) = NA_x NA_y + \text{const} \qquad \text{(Eq.29)}$$

$$F_1(NA_x, NA_y) = NA_x|NA_y| + \text{const} \qquad \text{(Eq. 30)}$$

$$F_2(NA_x, NA_y) = NA_x^2 + \text{const} \qquad \text{(Eq. 31)}$$

$$F_2(NA_x, NA_y) = NA_x^2 + NA_y^2 + \text{const} \qquad \text{(Eq.32)}$$

In embodiments, the $F_1$ type masks may be fabricated in a permanent configuration, such as a dedicated phase mask. For example, a dedicated phase mask may include a piece of glass with a pre-determined distribution of phase modulation such as glass with a fabricated thickness. In embodiments, the $F_2$ profile may be obtained using toric lenses, cylindrical plano-convex lenses, or the like.

In embodiments, one may realize an $F_2$-type mask using a defocused pupil-plane apodizer. The defocused phase effect may read as follows:

$$\frac{\delta}{\lambda}\sqrt{1 - NA_x^2 - NA_y^2} \approx \frac{\delta}{\lambda}\left(1 - \frac{NA_x^2}{2} - \frac{NA_y^2}{2}\right) \qquad \text{(Eq. 33)}$$

which is equivalent to an $F_2$-type mask with $$nh = \frac{\delta}{2}.$$

By taking pupil images with various defocus adjustment values S, one may evaluate overlay with multiple "effective" phase masks.

In embodiments, the system 100 is configured to receive the pupil images at various/different spot locations (e.g., three or more) on the overlay target. The dependence on spot location can be reduced using such a step.

The fit of the pupil images may include multiple fits configured to simultaneously solve for an effective mask height (nh), an optical stack thickness ($\Delta$), and the overlay measurement. For instance, the controller may be further configured to reduce Tool Induced Shift (TIS) error by performing a best fit scan for the effective mask height (nh), the optical stack thickness ($\Delta$), and the overlay measurement (when the known phase distribution is of the F1 type or the F2 type). The multiple fits may scan a parameter space of the nh and the $\Delta$. Two key input parameters for the intensity fit functions may include the effective mask height (n h) and the optical stack thickness ($\Delta$). The true values of these quantities are subject to fluctuation from the quoted ones due to process variation, erosion, and mis-calibration. This reduces the goodness-of-fit, and may result in inaccurate overlay estimates. To overcome this problem multiple fits may be performed. For example, the system 100 may be configured to scan the (nh, $\Delta$) parameter-space. The best fit may occur at the point (or close to the point) of the true (nh, $\Delta$), giving a simultaneous result for the (nh, $\Delta$, overlay measurement). This may be useful in measuring stack thicknesses, and in reducing metrology tool error (e.g., Tool Induced Shift (TIS)), for which nh may change.

Figure 4:
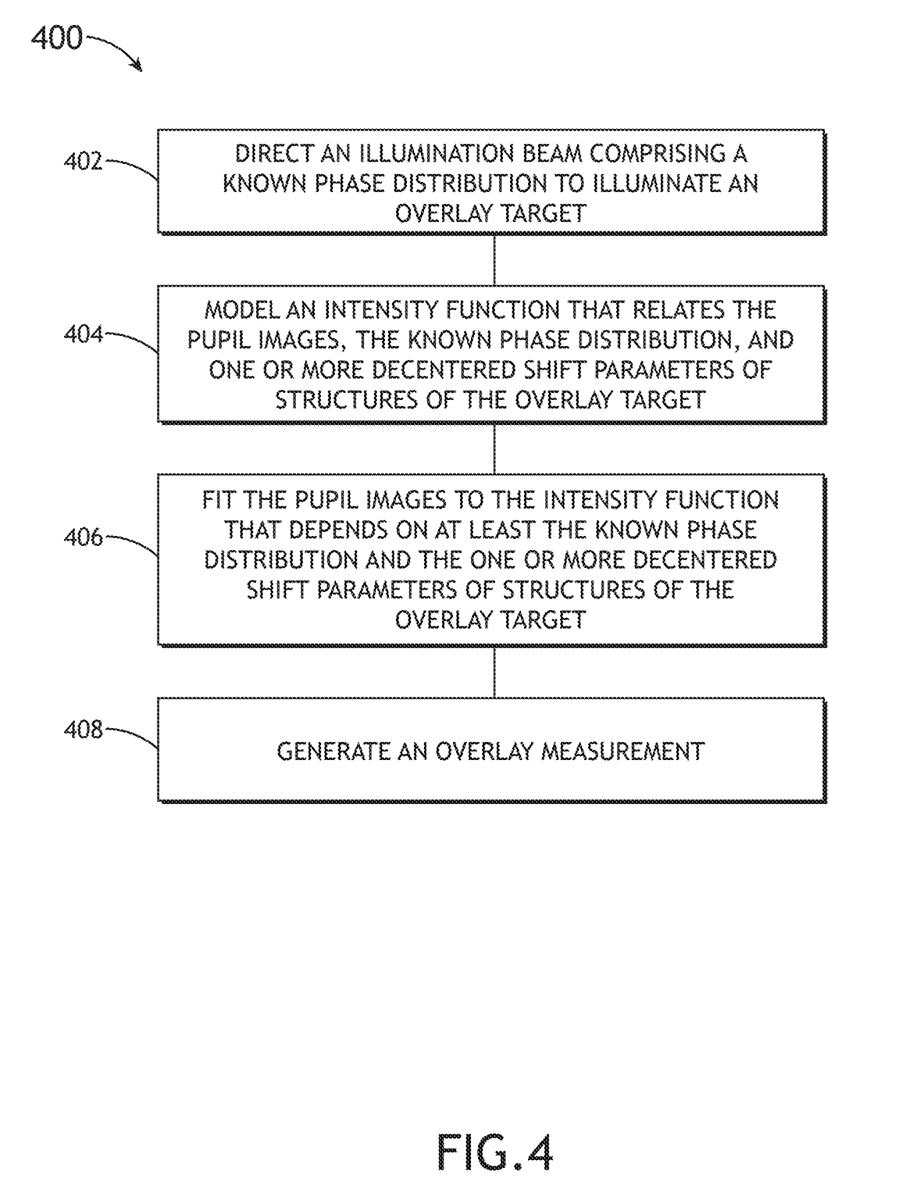
FIG. 4 is a flowchart of a method for overlay metrology, in accordance with one or more embodiments of the present disclosure.

FIG. 4 illustrates a flowchart of a method 400 for overlay metrology, in accordance with one or more embodiments of the present disclosure. It is noted that the embodiments and enabling technologies described previously herein in the context of the system 100 should be interpreted to extend to the method 400. It is further noted herein that the steps of method 400 may be implemented all or in part by system 100. It is further recognized, however, that the method 400 is not limited to the system 100 in that additional or alternative system-level embodiments may carry out all or part of the steps of method 400.

In step 402, an illumination beam 108 with a known phase distribution is directed (e.g., aimed, generated) to illuminate an overlay target 202. For example, a phase mask 148 in a pupil plane 120 may be used to induce the known phase distribution in the illumination beam 108. For example, the phase mask 148 may cause the known phase distribution based on prior knowledge (e.g., prior calibration, prior light wave simulation, and/or the like) of the phase mask 148. For instance, the phase mask 148 may be of the F1 or F2 type, and/or any other phase function. For instance, a phase mask 148 may be expected to generate a pattern in received pupil images that is indicative of a given amount of overlay, such as zero overlay.

In a step (e.g., additional step, step 402), the known phase distribution configured to be introduced to the illumination beam is received. For example, the controller 122 may receive values indicative of the type (e.g., F1 type) of known phase distribution and/or any other parameters (e.g., a thickness profile of the phase mask 148 being used in the system 100, the number and amount/magnitude of the defocus adjustments to be made, and/or the like) of a known phase distribution or used to calculate/receive a known phase distribution. For example, the known phase distribution may be fixed (e.g., built into the system 100 and stored on memory 126). The known phase distribution may be dynamic (e.g., the system configured to receive removably couplable phase masks in the illumination pathway with, for instance, known/measured/simulated known phase distributions; dynamically programmable defocus adjustments; both; and/or the like). For instance, the system 100 may be configured to sense (and/or a user may input) values to the controller 122 indicate of a known phase distribution (or phase mask 148) in use. For instance, the system 100 may be configured to calculate a known phase distribution based on system parameters (e.g., amount of defocus and/or profile of a phase mask 148) of the system 100.

In a step (e.g., additional step), pupil images of collected light 138 emanating from the overlay target 202 are received. For example, the detector 112 may receive the pupil images and/or the controller 122 may receive data indicative of the pupil images. The detector 112 may be located at a pupil plane 114. The detector 112 may be located near a pupil plane 114 (e.g., between a pupil plane 114 and a field plane 150; with 90% or more pupil plane conditions of the collection light 138; and/or the like). For example, the controller 122 may receive the pupil images and/or the controller 122 may receive data indicative of the pupil images.

In step 404, an intensity function that relates the pupil images, the known phase distribution, and one or more decentered shift parameters of structures of the overlay target 202 is modeled. For example, the intensity function may be modeled (e.g., equal to, derived from mathematically, simulated using, and/or the like) using Eq. 1 and/or Eq. 2 from the present disclosure.

In step 406, the pupil images are fit to an intensity function (e.g., one or more functions of the present disclosure such as Eq. 1 and Eq. 2 and the other equations herein) that depends on at least the known phase distribution and one or more decentered shift parameters (e.g., $x_T$ and $x_B$) of structures (e.g., gratings 208, 212) of the overlay target 202. The fit could involve calculating a difference or a ratio, inputting known values, and/or computing a correlation coefficient or a similarity measure between the pupil images and pupil images predicted for a given overlay value using the intensity function. For example, the one or more decentered shift parameters may be two or more decentered shift parameters.

In step 408, an overlay measurement is determined based on the fit of step 406. The overlay measurement can be (and/or be based on) a quantitative measure of the difference or similarity between the pupil images and pupil images predicted for a given overlay value using the intensity function. This can be obtained through various methods such as direct calculation, statistical modeling, machine learning, or other computational methods. It provides a measure of how accurately the process being controlled has produced the expected device features (e.g., gratings 208, 212).

The overlay measurement can be given in various units of measure. It could represent a physical distance such as the displacement between the actual and expected patterns or their shapes. Alternatively, it could be a dimensionless measure such as a correlation coefficient, a similarity index, a probability, or a confidence level.

In another step (not shown), one or more processes of a manufacturing of samples 104 are controlled based on the overlay measurement. This may involve adjusting the parameters of the process (such as temperature, pressure, time, flowrate, concentration, intensity, or frequency) in order to minimize the overlay. The adjustments could be made manually by an operator, or automatically by a control system in response to the overlay measurement.

For example, if the overlay measurement is greater than a predetermined threshold, then the process parameter(s) might be adjusted to reduce the overlay. Conversely, if the overlay measurement is less than the threshold, then the process parameter(s) might be left unchanged, or possibly adjusted to decrease the overlay slightly in order to keep it within an optimal range.

Such processes could include semiconductor manufacturing, photolithography, and many others.

In embodiments, the fit is based on a linear-regression pattern fitting. The linear-regression pattern fitting may involve fitting a straight line to data points representing the pupil images. This may be done using the least squares method or any other suitable fitting method. The slope, intercept, and other parameters of the fitted line may provide numerical values that can be used as parameters in the intensity function. This approach may allow for a more accurate and detailed description of the pupil images, which can improve the precision of the overlay measurement.

In embodiments, the fit is based on a calibration of the phase mask 148. The calibration process could involve adjusting the phase mask 148 to match a known standard or reference, and/or calibrating the system 100 to perform a fit for a given phase mask (i.e., so that the pupil images may be correlated to a corresponding overlay value). This could be done using a variety of techniques, such as using calibration pupil images of a calibration target comprising a known overlay as a reference and comparing the pupil images to the calibration pupil images and determining the overlay measurement based on a difference of the comparison.

For example, the calibration of the phase mask may include receiving calibration pupil images of a calibration target comprising a known overlay and determining a calibration associated with the phase mask 148. This can be used to calibrate the system 100 to know that specific pupil images match/correspond to specific overlay measurement values.

In embodiments, the overlay metrology system 100 further includes performing a defocus adjustment of the overlay target before/while receiving the pupil images, where the fit is based on an amount of the defocus adjustment performed. The defocus adjustment can cause the pupil images to blur, shift, or otherwise change in a way that can be quantified and used as a parameter during a fit of the intensity function. In embodiments, although not necessarily required, the receiving of the pupil images could include receiving a plurality of pupil images of a plurality of spot locations of the cell of the overlay target 202, where the fit is based on the plurality of pupil images. This may improve accuracy further.

In embodiments, the fit comprises a first pattern fitting and a second pattern fitting. For example, referring to FIG. 3, the first pattern may be based on a first order diffraction overlap region 308a of the pupil images, where the second pattern fitting is based on a second order diffraction overlap region 308b of the pupil images. For instance, the first order diffraction overlap region 308a, a first pattern fitting, and one of the (+1 first order diffraction intensity function or the −1 first order diffraction intensity function) may correspond with each other. Similar correspondence may exist for the second order diffraction overlap region 308b and a remaining one of the (+1 first order diffraction intensity function or the −1 first order diffraction intensity function).

Referring again to FIGS. 1A-3, various components are described in greater detail in accordance with one or more embodiments of the present disclosure.

The one or more processors 124 of the controller 122 may include any processor or processing element known in the art. For the purposes of the present disclosure, the term "processor" or "processing element" may be broadly defined to encompass any device having one or more processing or logic elements (e.g., one or more micro-processor devices, one or more application specific integrated circuit (ASIC) devices, one or more field programmable gate arrays (FPGAs), or one or more digital signal processors (DSPs)). In this sense, the one or more processors 124 may include any device configured to execute algorithms and/or instructions (e.g., program instructions stored in memory). In embodiments, the one or more processors 124 may be embodied as a desktop computer, mainframe computer system, workstation, image computer, parallel processor, networked computer, or any other computer system configured to execute a program configured to operate or operate in conjunction with the system 100, as described throughout the present disclosure. Moreover, different subsystems of the system 100 may include a processor or logic elements suitable for carrying out at least a portion of the steps described in the present disclosure. Therefore, the above description should not be interpreted as a limitation on the embodiments of the present disclosure but merely as an illustration. Further, the steps described throughout the present disclosure may be carried out by a single controller or, alternatively, multiple controllers. Additionally, the controller 122 may include one or more controllers housed in a common housing or within multiple housings. In this way, any controller or combination of controllers may be separately packaged as a module suitable for integration into system 100. Further, the controller 122 may analyze or otherwise process data received from the one or more detectors 112 and feed the data to additional components within the system 100 or external to the system 100.

Further, the memory device 126 may include any storage medium known in the art suitable for storing program instructions executable by the associated one or more processors 124. For example, the memory device 126 may include a non-transitory memory medium. As an additional example, the memory device 126 may include, but is not limited to, a read-only memory, a random-access memory, a magnetic or optical memory device (e.g., disk), a magnetic tape, a solid-state drive and the like. It is further noted that memory device 126 may be housed in a common controller housing with the one or more processors 124.

In this regard, the controller 122 may execute any of various processing steps associated with overlay metrology. For example, the controller 122 may be configured to generate control signals to direct or otherwise control the optical sub-system 102, or any components thereof. For instance, the controller 122 may be configured to receive signals corresponding to the pupil images from the one or more detectors 112. By way of another example, the controller 122 may generate correctables for one or more additional fabrication tools as feedback and/or feed-forward control of the one or more additional fabrication tools based on overlay measurements from the optical sub-system 102.

In embodiments, the controller 122 captures the pupil images detected by the one or more detectors 112. The controller 122 may capture data such as, but not limited to, the magnitudes or the phases of the pupil images using any technique known in the art such as, but not limited to, one or more phase-locked loops. Further, the controller 122 may capture the pupil images (e.g., detection signals), or any data associated with the pupil images, using any combination of hardware (e.g., circuitry) or software techniques.

In embodiments, the controller 122 generates (or determines) an overlay measurement between layers of an overlay target 202 (e.g., the first layer 210 and the second layer 214).

Further, the controller 122 may calibrate or otherwise modify the overlay measurement based on known, assumed, or measured features of the sample that may also impact the pupil images such as, but not limited to, sidewall angles or other sample asymmetries.

Referring again to FIG. 1B, various components of the optical sub-system 102 are described in greater detail in accordance with one or more embodiments of the present disclosure.

In embodiments, the illumination sub-system 106 includes an illumination source 128 configured to generate at least one illumination beam 108. The illumination from the illumination source 128 may include one or more selected wavelengths of light including, but not limited to, ultraviolet (UV) radiation, visible radiation, or infrared (IR) radiation.

The illumination source 128 may include any type of illumination source suitable for providing at least one illumination beam 108. In embodiments, the illumination source 128 is a laser source. For example, the illumination source 128 may include, but is not limited to, one or more narrowband laser sources, a broadband laser source, a supercontinuum laser source, a white light laser source, or the like. In this regard, the illumination source 128 may provide an illumination beam 108 having high coherence (e.g., high spatial coherence and/or temporal coherence). In embodiments, the illumination source 128 includes a laser-sustained plasma (LSP) source. For example, the illumination source 128 may include, but is not limited to, a LSP lamp, a LSP bulb, or a LSP chamber suitable for containing one or more elements that, when excited by a laser source into a plasma state, may emit broadband illumination.

In embodiments, the illumination sub-system 106 includes one or more optical components suitable for modifying and/or conditioning the illumination beam 108 as well as directing the illumination beam 108 to the sample 104. For example, the illumination sub-system 106 may include one or more illumination lenses 130 (e.g., to collimate the illumination beam 108, to relay an illumination pupil plane 120 and/or an illumination field plane 132, or the like). In embodiments, the illumination sub-system 106 includes one or more illumination control optics 134 to shape or otherwise control the illumination beam 108. For example, the illumination control optics 134 may include, but are not limited to, one or more field stops, one or more pupil stops, one or more polarizers, one or more filters, one or more beam splitters, one or more diffusers, one or more homogenizers, one or more apodizers, one or more beam shapers, or one or more mirrors (e.g., static mirrors, translatable mirrors, scanning mirrors, or the like).

In embodiments, the illumination sub-system 106 illuminates the sample 104 with two or more illumination beams 108. Further, the two or more illumination beams 108 may be, but are not required to be, incident on different portions of the sample 104 (e.g., different cells 204 of an overlay target 202) within a measurement field of view (e.g., a field of view of the objective lens 136). It is contemplated herein that the two or more illumination beams 108 may be generated using a variety of techniques. In embodiments, the illumination sub-system 106 includes two or more apertures at an illumination field plane 132. In embodiments, the illumination sub-system 106 includes one or more beamsplitters to split illumination from the illumination source 128 into the two or more illumination beams 108. In embodiments, at least one illumination source 128 generates two or more illumination beams 108 directly. In a sense, each illumination beam 108 may be considered to be a part of a different illumination channel regardless of the technique in which the various illumination beams 108 are generated.

The collection sub-system 110 may include one or more optical elements suitable for modifying and/or conditioning the collected light 138 from the sample 104. In embodiments, the collection sub-system 110 includes one or more collection lenses 140 (e.g., to collimate the illumination beam 108, to relay pupil and/or field planes, or the like), which may include, but are not required to include, the objective lens 136. In embodiments, the collection sub-system 110 includes one or more collection control optics 142 to shape or otherwise control the collected light 138. For example, the collection control optics 142 may include, but are not limited to, one or more field stops, one or more pupil stops, one or more polarizers, one or more filters, one or more beam splitters, one or more diffusers, one or more homogenizers, one or more apodizers, one or more beam shapers, or one or more mirrors (e.g., static mirrors, translatable mirrors, scanning mirrors, or the like). In another example, the collection sub-system 110 may include one or more collection field planes 150. Note that the position of the phase mask may be placed before and/or after the collection control optics 142 and/or one or more collection lenses 140 and is not limited by the positions shown in FIG. 1B or FIG. 1C.

In embodiments, the collection sub-system 110 includes two or more collection channels 144, each with a separate detector 112 (or multiple detectors 112). For example, the optical sub-system 102 may include one or more beamsplitters 146 arranged to split the collected light 138 into the collection channels 144. Further, the beamsplitters 146 may be polarizing beamsplitters, non-polarizing beamsplitters, or a combination thereof.

In embodiments, multiple collection channels 144 are configured to collect light from multiple illumination beams 108 on the sample 104. For example, in the case that an overlay target 202 has two or more cells, the optical sub-system 102 may simultaneously illuminate the different cells 204 with different illumination beams 108 and simultaneously capture detection signals associated with each illumination beam 108. Additionally, in embodiments, multiple illumination beams 108 directed to the sample 104 may have different polarizations. In this way, the diffraction orders associated with each of the illumination beams 108 may be separated. For example, polarizing beamsplitters 146 may efficiently separate the diffraction orders associated with the different illumination beams 108. By way of another example, polarizers may be used in one or more collection channels 144 to isolate desired diffraction orders for measurement.

Referring again to FIG. 1A, it is noted herein that the one or more components of system 100 may be communicatively coupled to the various other components of system 100 in any manner known in the art. For example, the one or more processors 124 may be communicatively coupled to each other and other components via a wireline (e.g., copperwire, fiber optic cable, and the like) or wireless connection (e.g., RF coupling, IR coupling, WiMax, Bluetooth, 3G, 4G, 4G LTE, 5G, and the like). By way of another example, the controller 122 may be communicatively coupled to one or more components of optical sub-system 102 via any wireline or wireless connection known in the art.

In embodiments, the one or more processors 124 may include any one or more processing elements known in the art. In this sense, the one or more processors 124 may include any microprocessor-type device configured to execute software algorithms and/or instructions. In embodiments, the one or more processors 124 may consist of a desktop computer, mainframe computer system, workstation, image computer, parallel processor, or other computer system (e.g., networked computer) configured to execute a program configured to operate the system 100, as described throughout the present disclosure. It should be recognized that the steps described throughout the present disclosure may be carried out by a single computer system or, alternatively, multiple computer systems. Furthermore, it should be recognized that the steps described throughout the present disclosure may be carried out on any one or more of the one or more processors 124. In general, the term "processor" may be broadly defined to encompass any device having one or more processing elements, which execute program instructions from memory 126. Moreover, different subsystems of the system 100 may include processor or logic elements suitable for carrying out at least a portion of the steps described throughout the present disclosure. Therefore, the above description should not be interpreted as a limitation on the present disclosure but merely an illustration.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken as limiting.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary.

The previous description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

All of the methods described herein may include storing results of one or more steps of the method embodiments in memory. The results may include any of the results described herein and may be stored in any manner known in the art. The memory may include any memory described herein or any other suitable storage medium known in the art. After the results have been stored, the results can be accessed in the memory and used by any of the method or system embodiments described herein, formatted for display to a user, used by another software module, method, or system, and the like. Furthermore, the results may be stored "permanently," "semi-permanently," temporarily," or for some period of time. For example, the memory may be random access memory (RAM), and the results may not necessarily persist indefinitely in the memory.

It is further contemplated that each of the embodiments of the method described above may include any other step(s) of any other method(s) described herein. In addition, each of the embodiments of the method described above may be performed by any of the systems described herein.

The herein described subject matter sometimes illustrates different components contained within, or connected with, other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected," or "coupled," to each other to achieve the desired functionality, and any two components capable of being so associated can also be viewed as being "couplable," to each other to achieve the desired functionality. Specific examples of couplable include but are not limited to physically mateable and/or physically interacting components and/or wirelessly interactable and/or wirelessly interacting components and/or logically interacting and/or logically interactable components.

Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," and the like). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, and the like" is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, and the like). In those instances where a convention analogous to "at least one of A, B, or C, and the like" is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, and the like). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

We claim:

1. An overlay metrology system comprising:
   a controller including one or more processors configured to execute program instructions causing the one or more processors to:
   receive pupil images of collected light emanating from an overlay target and receive a known phase distribution configured to be introduced to an illumination beam directed at the overlay target;
   model an intensity function that relates the pupil images, the known phase distribution, and one or more decentered shift parameters of structures of the overlay target;
   fit the pupil images to the intensity function that depends on at least the known phase distribution and the one or more decentered shift parameters of structures of the overlay target; and
   generate an overlay measurement based on the fit.

2. The overlay metrology system of claim 1, wherein the overlay target is a single cell overlay target.

3. The overlay metrology system of claim 1, wherein the fit comprises a linear-regression pattern fitting.

4. The overlay metrology system of claim 1, wherein the fit comprises a first pattern fitting and a second pattern fitting, wherein the first pattern fitting is based on a first order diffraction overlap region of the pupil images, wherein the second pattern fitting is based on a second order diffraction overlap region of the pupil images.

5. The overlay metrology system of claim 1, wherein the fit is based on a calibrating of a phase mask configured to cause the known phase distribution.

6. The overlay metrology system of claim 1, wherein the overlay target comprises at least one of: a Moiré fringe overlay target or a common-pitch overlay target.

7. The overlay metrology system of claim 1, further comprising performing a defocus adjustment of the overlay target, wherein the fit is based on an amount of the defocus adjustment performed, wherein the known phase distribution is based on the amount of the defocus adjustment performed.

8. The overlay metrology system of claim 7, wherein the receiving the pupil images comprises performing a plurality of defocus adjustments of the overlay target.

9. The overlay metrology system of claim 1, wherein the receiving the pupil images comprises receiving a plurality of pupil images of a plurality of spot locations of a cell of the overlay target; and wherein the fit is based on the plurality of pupil images.

10. The overlay metrology system of claim 1, wherein the known phase distribution comprises an F1 type phase distribution which is wavelength-independent and characterizable in a form of at least one of:

$$F_1(NA_x, NA_y) = NA_x NA_y + \text{constant; or}$$

$$F_1(NA_x, NA_y) = NA_x |NA_y| + \text{constant.}$$

11. The overlay metrology system of claim 10, wherein the introduction of the known phase distribution to the illumination beam is performed via a phase mask of the F1 type phase distribution of the system.

12. The overlay metrology system of claim 10, wherein the fit of the pupil images to the intensity function is performed simultaneously for a +1 first order diffraction intensity function and a −1 first order diffraction intensity function for the F1 type phase distribution.

13. The overlay metrology system of claim 1, wherein the known phase distribution comprises an F2 type phase distribution which is wavelength-independent and characterizable in a form of at least one of:

$$F_2(NA_x, NA_y) = NA_x^2 + \text{constant; or}$$

$$F_2(NA_x, NA_y) = NA_x^2 + NA_y^2 + \text{constant.}$$

14. The overlay metrology system of claim 13, wherein the introduction of the known phase distribution to the illumination beam is performed via a phase mask of the F2 type phase distribution of the system.

15. The overlay metrology system of claim 13, wherein the fit of the pupil images to the intensity function is performed sequentially for a +1 first order diffraction intensity function and a −1 first order diffraction intensity function for the F2 type phase distribution.

16. The overlay metrology system of claim 15, wherein the phase mask of the F2 type phase distribution comprises at least one of:

a toric lens;
a cylindrical plano-convex lens; or
a defocused pupil-plane apodizer.

17. The overlay metrology system of claim 1, wherein the fit of the pupil images comprises multiple fits configured to simultaneously solve for an effective mask height (nh), an optical stack thickness (Δ), and the overlay measurement, the multiple fits scanning a parameter space of the nh and the Δ.

18. An overlay metrology system comprising:
an optical sub-system comprising:
an illumination source configured to generate an illumination beam;
an objective lens configured to direct the illumination beam to an overlay target of a sample;
a phase mask configured to cause a known phase distribution in a portion of the illumination beam;
a detector configured to receive pupil images of collected light emanating from the overlay target; and
a controller communicatively coupled to the detector, the controller including one or more processors configured to execute program instructions causing the one or more processors to:
receive the pupil images of the collected light emanating from the overlay target and receive the known phase distribution configured to be introduced to the portion of the illumination beam directed at the overlay target;
model an intensity function that relates the pupil images, the known phase distribution, and one or more decentered shift parameters of structures of the overlay target;
fit the pupil images to the intensity function that depends on at least the known phase distribution and the one or more decentered shift parameters of structures of the overlay target; and;
generate an overlay measurement based on the fit.

19. The overlay metrology system of claim 18, wherein the overlay target is a single cell overlay target.

20. The overlay metrology system of claim 18, wherein the fit comprises a linear-regression pattern fitting.

21. The overlay metrology system of claim 18, wherein the fit comprises a first pattern fitting and a second pattern fitting, wherein the first pattern fitting is based on a first order diffraction overlap region of the pupil images, wherein the second pattern fitting is based on a second order diffraction overlap region of the pupil images.

22. The overlay metrology system of claim 18, wherein the fit is based on a calibrating of the phase mask configured to cause the known phase distribution.

23. The overlay metrology system of claim 18, wherein the overlay target comprises at least one of: a Moiré fringe overlay target or a common-pitch overlay target.

24. The overlay metrology system of claim 18, further comprising performing a defocus adjustment of the overlay target, wherein the fit is based on an amount of the defocus adjustment performed, wherein the known phase distribution is based on the amount of the defocus adjustment performed.

25. The overlay metrology system of claim 24, wherein the receiving the pupil images comprises performing a plurality of defocus adjustments of the overlay target.

26. The overlay metrology system of claim 18, wherein the receiving the pupil images comprises receiving a plurality of pupil images of a plurality of spot locations of a cell of the overlay target; and wherein the fit is based on the plurality of pupil images.

27. A method comprising:
directing an illumination beam comprising a known phase distribution to illuminate an overlay target;
receiving pupil images of collected light emanating from the overlay target;
modeling an intensity function that relates the pupil images, the known phase distribution, and one or more decentered shift parameters of structures of the overlay target;
fitting the pupil images to the intensity function that depends on at least the known phase distribution and the one or more decentered shift parameters of structures of the overlay target; and
generating an overlay measurement based on the fit.

28. The method of claim 27, wherein the overlay target is a single cell overlay target.

29. The method of claim 27, wherein the fit comprises a linear-regression pattern fitting.

30. The method of claim 27, wherein the fit comprises a first pattern fitting and a second pattern fitting, wherein the first pattern fitting is based on a first order diffraction overlap region of the pupil images, wherein the second pattern fitting is based on a second order diffraction overlap region of the pupil images.

31. The method of claim 27, wherein the fit is based on a calibrating of a phase mask configured to cause the known phase distribution.

32. The method of claim 27, wherein the overlay target comprises at least one of: a Moiré fringe overlay target or a common-pitch overlay target.

33. The method of claim 27, further comprising performing a defocus adjustment of the overlay target, wherein the fit is based on an amount of the defocus adjustment performed, wherein the known phase distribution is based on the amount of the defocus adjustment performed.

34. The method of claim 33, wherein the receiving the pupil images comprises performing a plurality of defocus adjustments of the overlay target.

35. The method of claim 27, wherein the receiving the pupil images comprises receiving a plurality of pupil images of a plurality of spot locations of a cell of the overlay target; and wherein the fit is based on the plurality of pupil images.

36. The method of claim 27, wherein the known phase distribution comprises an F1 type phase distribution which is wavelength-independent and characterizable in a form of at least one of:

$$F_1(NA_x, NA_y) = NA_x NA_y + \text{constant; or}$$

$$F_1(NA_x, NA_y) = NA_x |NA_y| + \text{constant.}$$

37. The method of claim 36, wherein an introduction of the known phase distribution to the illumination beam is performed via a phase mask of the F1 type phase distribution.

38. The method of claim 27, wherein the known phase distribution comprises an F2 type phase distribution which is wavelength-independent and characterizable in a form of at least one of:

$$F_2(NA_x, NA_y) = NA_x^2 + \text{constant; or}$$

$$F_2(NA_x, NA_y) = NA_x^2 + NA_y^2 + \text{constant.}$$

* * * * *